United States Patent [19]
Haugland et al.

[11] Patent Number: 5,723,218
[45] Date of Patent: Mar. 3, 1998

[54] DIPYRROMETHENEBORON DIFLUORIDE LABELED FLOURESCENT MICROPARTICLES

[75] Inventors: Richard P. Haugland; Rosaria P. Haugland, both of Eugene; John Michael Brinkley, Elmira; Hee Chol Kang; Michael Kuhn, both of Eugene, all of Oreg.; K. Sam Wells, Vacaville, Calif.; Yu Zhong Zhang, Eugene, Oreg.

[73] Assignee: Molecular Probes, Inc., Eugene, Oreg.

[21] Appl. No.: 484,151

[22] Filed: Jun. 7, 1995

(Under 37 CFR 1.47)

Related U.S. Application Data

[63] Continuation-in-part of Ser. No. 629,466, Dec. 18, 1990, abandoned, Ser. No. 843,360, Feb. 25, 1992, Pat. No. 5,453,517, Ser. No. 28,319, Mar. 8, 1993, Pat. No. 5,442,045, Ser. No. 375,360, Jan. 19, 1995, Pat. No. 5,516,864, Ser. No. 45,758, Apr. 8, 1993, Pat. No. 5,451,663, Ser. No. 246,790, May 20, 1994, Pat. No. 5,433,896, Ser. No. 246,847, May 20, 1994, Pat. No. 5,459,276, Ser. No. 247,013, May 20, 1994, Pat. No. 5,501,980, Ser. No. 247,108, May 20, 1994, Pat. No. 5,573,909, and Ser. No. 384,945, Feb. 6, 1995, said Ser. No. 28,319, is a division of Ser. No. 509,360, Apr. 16, 1990, Pat. No. 5,227,487, said Ser. No. 372,536, is a division of Ser. No. 38,918, Mar. 29, 1993, Pat. No. 5,405,975, said Ser. No. 45,758, is a division of Ser. No. 786,767, Nov. 1, 1991, Pat. No. 5,274,113, said Ser. No. 247,108, is a continuation-in-part of Ser. No. 882,299, May 13, 1992, Pat. No. 5,326,692.

[51] Int. Cl.$^6$ .................................................. B32B 27/18
[52] U.S. Cl. .......................... 428/402; 428/403; 428/407; 548/405
[58] Field of Search .................................. 428/402, 403, 428/407; 548/405

[56] References Cited

U.S. PATENT DOCUMENTS

| | | | |
|---|---|---|---|
| 2,994,697 | 8/1961 | Eckert et al. | 546/52 |
| 3,096,333 | 7/1963 | Wilson et al. | 546/100 |
| 3,857,931 | 12/1974 | Hager | 436/509 |
| 4,046,723 | 9/1977 | Dorman | 524/498 |

(List continued on next page.)

FOREIGN PATENT DOCUMENTS

| | | |
|---|---|---|
| 0 407 188 A1 | 1/1991 | European Pat. Off. . |
| 2 277 096 | 10/1994 | United Kingdom . |
| WO 93/06482 | 4/1993 | WIPO . |
| WO 94/24213 | 10/1994 | WIPO . |

OTHER PUBLICATIONS

Jett, Keller, Martin, Nguyen, & Saunders, *Ultrasensitive Molecular–Level Flow Cytometry*, Flow Cytometry and Sorting, p. 381 (2nd ed., Wiley–Liss Inc., NY 1990).

Hook & Odeyale, *Confocal Scanning Fluorescence Microscopy: A New Method for Phagocytosis Research*, J. Leukocyte Biol., 45, 277 (1989).

(List continued on next page.)

*Primary Examiner*—D. S. Nakarani
*Attorney, Agent, or Firm*—Allegra J. Helfenstein; Anton E. Skaugset

[57] ABSTRACT

The invention is a novel fluorescently labeled microparticle, where the microparticle internally incorporates at least one dipyrromethboron difluoride dye. Appropriate selection of substituents results in dipyrromethboron difluoride derivatives that, when incorporated into polymer microparticles, give the desired excitation and emission wavelengths. The spectral characteristics of the labeling dyes in liquid are not greatly changed when the dye is incorporated into the particles, and the spectral excitation and emission wavelengths are compatible with commonly used filter sets. Other embodiments of the fluorescent microparticles include additional dyes and/or bioreactive substances.

30 Claims, 4 Drawing Sheets

U.S. PATENT DOCUMENTS

| | | | |
|---|---|---|---|
| 4,326,008 | 4/1982 | Rembaum | 428/403 |
| 4,421,896 | 12/1983 | Dorman | 525/54.1 |
| 4,774,339 | 9/1988 | Haugland et al. | 548/405 |
| 4,808,524 | 2/1989 | Snyder et al. | 435/36 |
| 4,916,711 | 4/1990 | Boyer et al. | 372/53 |
| 4,945,171 | 7/1990 | Haugland et al. | 549/224 |
| 5,187,288 | 2/1993 | Kang et al. | 548/110 |
| 5,227,487 | 7/1993 | Haugland et al. | 546/15 |
| 5,248,782 | 9/1993 | Haugland et al. | 548/110 |
| 5,268,486 | 12/1993 | Waggoner et al. | 548/427 |
| 5,274,113 | 12/1993 | Kang et al. | 548/405 |
| 5,316,906 | 5/1994 | Haugland et al. | 435/4 |
| 5,321,130 | 6/1994 | Yue et al. | 536/23.1 |
| 5,326,692 | 7/1994 | Brinkley et al. | 435/6 |
| 5,338,854 | 8/1994 | Kang et al. | 548/405 |
| 5,405,975 | 4/1995 | Kuhn et al. | 549/347 |
| 5,410,030 | 4/1995 | Yue et al. | 536/23.1 |
| 5,433,896 | 7/1995 | Kang et al. | 252/700 |

OTHER PUBLICATIONS

Carrington, Fogarty, Lifshitz, & Fay, *Three–Dimensional Imaging on Confocal and Wide–Field Microscopes*, Handbook of Biological Confocal Microscopy, Ch. 14, p. 154 (Rev. ed. J. Pawley, Plenum Press, NY 1990).

Treibs & Kreuzer, *Difluorboryl–Komplexe von Di–und Tripyrrylemethenen*, Liebigs Ann. Chem., 718, 208 (1968).

Bangs, *Uniform Latex Particles*, Ch. VII (1984 Seragen, Inc.).

Guilford, *Chemical Aspects of Affinity Chromatography*, Chem. Soc. Rev., 2, 249 (1973).

Nathan & Cohn, *Antitumor Effects of Hydrogen Peroxide in Vivo*, J. Exp. Med., 154, 1539–1553 Nov. 1981.

Pethig, Kuhn, Payne, Adler, Chen, & Jaffee, *On the Dissociation Constants of BAPTA–type Calcium Buffer*, Cell Calcium 10, 491 (1989).

DIPYRROMETHENEBORON DIFLUORIDE LABELED FLOURESCENT MICROPARTICLES

This application is a continuation-in-part of the following applications: Ser. No. 07/629,466, filed Dec. 18, 1990, now abandoned; Ser. No. 07/843,360, filed Feb. 25, 1992, now U.S. Pat. No. 5,453,517; Ser. No. 08/028,319, filed Mar. 8, 1993, now U.S. Pat. No. 5,442,045, which is a division of Ser. No. 07/509,360, filed Apr. 16, 1990, now U.S. Pat. No. 5,227,487; Ser. No. 08/375,360, filed Jan. 19, 1995, now U.S. Pat. No. 5,516,864, which is a division of Ser. No. 08/038,918, filed Mar. 29, 1993, now U.S. Pat. No. 5,405,975; Ser. No. 08/045,758, filed Apr. 8, 1993, now U.S. Pat. No. 5,451,663,which is a division of Ser. No. 07/786,767, filed Nov. 1, 1991, now U.S. Pat. No. 5,274,113; Ser. No. 08/246,790, filed May 20, 1994 now U.S. Pat. No. 5,433,896; Ser. No. 08/246,847, filed May 20, 1994, now U.S. Pat. No. 5,459,276; Ser. No. 08/247,013, filed May 20, 1994, now U.S. Pat. No. 5,501,980; Ser. No. 08/247,108, filed May 20, 1994, now U.S. Pat. No. 5,573,909,which is a continuation-in-part of Ser. No. 07/882,299, filed May 13, 1992, now U.S. Pat. No. 5,326,692; and Ser. No. 08/384,945, filed Feb. 6, 1995, now allowed.

This invention was made in part with government support under R44 AI32831-03 awarded by the National Institutes of Health and under research contract no. N00014-C-0270 awarded by the U.S. Office of Naval Research. The U.S. government has certain rights in this invention.

FIELD OF THE INVENTION

The invention relates to microparticles labeled with fluorescent dyes. In particular, the invention describes polymer microparticles labeled with dipyrrometheneboron difluoride derivative compounds, optionally including additional dyes and/or bioreactive materials, for use in standardization of fluorescence-based instrumentation, as biological tracers and in the detection and analysis of biomolecules.

BACKGROUND OF THE INVENTION

Polymer microparticles labeled with fluorescent dyes (fluorescent microparticles) have found use in a wide variety of applications. Microparticles are generally considered to be spherical or irregular in shape, and to be less than about 50 micrometers in diameter. They may be prepared by several practical methods from a variety of polymerizable monomers, including styrenes, acrylates and unsaturated chlorides, esters, acetates, amides and alcohols. For example, Rembaum (U.S. Pat. No. 4,326,008 (1982)) discloses fluorescent microspheres obtained by copolymerizing an acrylic monomer containing a covalent bonding group such as hydroxyl, amine, or carboxyl with a fluorescent co-monomer such as dansyl allyl amine. Fluorescent microparticles are most commonly used in applications that can benefit from use of monodisperse, chemically inert, biocompatible particles that radiate detectable fluorescence and that can bind to a particular substance in the environment.

For example, fluorescent particles to which biological molecules have been attached have been used for immunoassays (U.S. Pat. No. 4,808,524 to Snyder, et al. (1989)), as labels for cell surface antigens (Jett, Keller, Martin, Nguyen, & Saunders, *Ultrasensitive Molecular-Level Flow Cytometry*, in FLOW CYTOMETRY AND SORTING, p. 381 (2nd ed., Wiley-Liss Inc., N.Y. 1990)), and as tracers to study cellular metabolic processes (Hook & Odeyale, *Confocal Scanning Fluorescence Microscopy: A New Method for Phagocytosis Research*, J. LEUKOCYTE BIOL. 45: 277 (1989)). The high surface area of microparticles provides an excellent matrix for attaching biological molecules while the fluorescent properties of these particles enable them to be detected with high sensitivity. They can be quantitated by their fluorescence either in aqueous suspension or when captured on membranes. Fluorescent microparticles can be visualized with a variety of imaging techniques, including ordinary light or fluorescence microscopy and laser scanning confocal microscopy. Three-dimensional imaging resolution techniques in confocal microscopy utilize knowledge of the microscope's point spread function (image of a point source) to place out-of-focus light in its proper perspective. Small, uniform fluorescent labeled polystyrene microspheres have been employed as point sources for these microscopes (Cartington, Fogarty, Lifshitz, & Fay, *Three-Dimensional Imaging on Confocal and Wide-Field Microscopes*, in HANDBOOK OF BIOLOGICAL CONFOCAL MICROSCOPY Ch. 14, p. 154 (Rev. ed. J. Pawley, Plenum Press, N.Y. 1990).

Although many luminescent compounds suitable for imparting bright and visually attractive colors to various cast or molded plastics such as polystyrene and polymethyl methacrylate, and uniform latex microspheres have been described in the patent literature U.S. Pat. No. 2,994,697 to Eckert, et al. (1961 ); U.S. Pat. No. 3,096,333 to Wilson, et al. (1963)), no derivatives of the dipyrrometheneboron difluoride family of compounds have been described as useful dyes for preparing fluorescent microparticles. This family of dyes possesses advantageous spectral data and other properties that result in superior fluorescent microparticles.

The fact that a dye is fluorescent does not mean that it is inherently suitable for labeling polymer microparticles. The principal dyes that have been reported for incorporation within the particle have been coumarin derivatives and aromatic hydrocarbons, both of which have typically broad emission excited in the ultraviolet to about 500 nm. In particular, nile red, which is excited in the visible with very broad spectra, is highly environment dependent and both its emission and excitation spectra are not very intense. Nile red, as well as 3-(2-benzothiazolyl)-diethylaminocoumarin (coumarin 6), 7-dimethylamino cyclopenta[c]-coumarin (coumarin 138), oxazine 170 and many other fluorescent dyes have spectral properties that are substantially altered by their inclusion into the solid phase of the polymer microparticles, i.e., their excitation and emission maxima and Stokes shift are substantially different from that observed in aqueous or alcoholic solutions. The fluorescence efficiency (quantum yield) of these dyes is reduced substantially and, in the case of the coumarins and Nile red, the excitation and emission wavelengths are blue-shifted, resulting in microparticles that have very different spectral properties than that observed in aqueous or alcoholic solution (see FIG. 2).

Photostability (resistance to loss of color and/or fluorescence upon prolonged irradiation with photons) of microparticles containing certain other dyes such as fluorescein and dansyl derivatives is poor, resulting in substantial loss of fluorescence in a matter of seconds. Photostability of the fluorescent microparticles during prolonged exposure by high-intensity irradiation at excitation wavelengths is particularly important when using the labeled microparticles for fluorescence microscopy. It is also important in fluorescence immunoassays, because the loss of fluorescence ultimately decreases sensitivity of the assay.

In addition to possessing photostability problems, cationic or anionic fluorescent dyes such as fluorescein or rhodamine 6G contribute to or alter the charge properties of the polymer microparticles. This can result in destabilization of the particles or can cause changes in surface properties that produce deviations from optimum binding of biomolecules. Preservation of surface properties is of crucial importance in immunodiagnostic applications, where biomolecules are attached to the microparticles.

Properties of the dyes also affect the process of manufacturing the labeled microparticles. If the dyes are to be incorporated into the polymer by stock dyeing methods (incorporation during the polymerization process), the dyes must be stable to free radicals and stable at the polymerization temperatures used in preparing the microparticles. If the dyes are to be incorporated in the interior of previously manufactured polymer microparticles, the dyes must be soluble in the latex but be insoluble or very slightly soluble in water so that they will not leach out of the particles when in aqueous suspension. If the dyes are to be covalently bonded to surface groups on the microparticles, the dyes must be freely soluble in the medium in which the particles are suspended and must have reactive functional groups capable of forming stable chemical bonds with the available surface groups on the microparticles.

Furthermore, the dyes should not be removable by commonly used solvents, especially water-based solvents. Fluorescein-, rhodamine- and oxazine 170-based fluorescent dyes that are readily soluble in water cannot be added to many kinds of previously manufactured microparticles to give stable, highly fluorescent particles with desired characteristics, as these dyes tend to leach out of the particles as a result of their high water solubility. Charged fluorophores such as fluorescein and rhodamine are also restricted to the surface of hydrophobic polymers such as polystyrene. Therefore, they are best incorporated into microparticles by copolymerizing the dye into the microparticle during manufacture or by reaction with groups on the surface. However, it is difficult and expensive to produce microparticles with many desirable characteristics using these methods.

What is needed is a microparticle labeled with a fluorescent dye that is very soluble in oil-based solvents and in the microparticles but sparingly soluble in water-based solvents, or that has the appropriate reactivity for chemical attachment to surface-modified microparticles, or that contains the appropriate reactivity for copolymerization. Furthermore, the dye should have excitation and emission wavelengths and spectral intensities that are not greatly reduced when the dye is in the polymer medium, have spectral excitation and emission wavelengths compatible with commonly used filter sets and have good photostability. In addition, it is important that the dye does not significantly change the net surface charge on the microparticles and does not significantly change the hydrophobic parking area (the area of the microparticle that is hydrophobic and that will readily bind to hydrophobic substances) of the microparticles. For applications as tracers and labeling reagents, it is usually preferred that the microparticles be as brightly fluorescent as possible, which is a combination of high optical absorbance (extinction coefficient) and high quantum yield. The invention of microparticles labeled with dipyrromethenoboron difluoride derivatives has all of these advantageous characteristics.

Certain characteristics of dipyrromethenoboron difluoride dyes are known. The fluorescence of simple substituted dipyrromethenoboron difluoride derivatives, comparable to that of fluorescein, was previously noted by Treibs & Kreuzer (*Difluorboryl-Komplexe von Di- und Tripyrrylmethenen*, LIEBIGS ANN. CHEM. 718, 208 (1968)). Use of such dyes for dye laser systems is described in U.S. Pat. No. 4,916,711 to Boyer, et al. (1990) (incorporated by reference). Chemically reactive dipyrromethenoboron difluoride dyes that can be coupled to other molecules are described in U.S. Pat. No. 4,774,339 to Haugland, et al. (1988) (incorporated by reference). These references describe some advantages of alkyl substituted dipyrromethenoboron difluoride derivative dyes, including high quantum yield, insensitivity of fluorescence properties to changes in pH, and a broad range of solubility. The references, however, do not mention or infer the advantages to be gained by incorporating the dyes in polymeric microparticles.

More recently, additional dipyrromethenoboron difluoride dyes that have advantageous long-wavelength characteristics have been discovered. Dipyrromethenoboron difluoride dyes that have advantageous long-wavelength characteristics not previously found in this class of dyes include ethenyl-substituted dipyrromethenoboron difluoride dyes described in U.S. Pat. No. 5,187,288 to Kang et al. (1993) (incorporated by reference); heteroaryl-substituted dipyrromethenoboron difluoride dyes described in U.S. Pat. No. 5,248,782 to Haugland, et al. (1993) (incorporated by reference); chemically reactive long wavelength dyes described in U.S. Pat. No. 5,274,113 to Kang, et al. (1993) (incorporated by reference); and benzo-substituted dipyrromethenoboron difluoride dyes described in U.S. Ser. No. 08/246,790 by Kang, et al. filed May 20, 1994 (incorporated by reference). These longer wavelength dipyrromethenoboron difluoride dyes are used alone or in combination with other dipyrromethenoboron difluoride dyes described above, optionally including other fluorescent dyes or bioreactive substances, for novel labeled microparticles. Mixtures of dyes where little to no energy transfer occurs, in contrast to the preferred embodiments of U.S. Pat. No. 5,326,692 (incorporated by reference), can be used to match the spectral characteristics of target materials (FIG. 3).

SUMMARY OF THE INVENTION

The invention describes a novel labeled polymer microparticle. The novel microparticle, labeled with derivatives of dipyrromethenoboron difluoride dyes (e.g. 4,4-difluoro-4-bora-3a,4a,-diaza-s-indacene derivatives), has greatly improved fluorescence properties compared to microparticles currently used that are labeled with other dyes (Table 3). The dyes are used to label any suitable polymer microparticles that have a diameter between about 0.01 micrometers and about 50 micrometers, with composition including, but not limited to, a variety of suitable commercially available polymerizable monomers, including styrenes, acrylates and unsaturated chlorides, esters, acetates, amides, alcohols, and glass.

The subject fluorescent microparticles can be prepared with a variety of surface properties, with functional groups including, but not limited to sulfate, phosphate, hydroxyl, carboxyl, ester, amide, amidine, amine, sulfhydryl and aldehyde. The subject fluorescent microparticles can be manufactured in a variety of useful sizes and shapes. Other embodiments of the fluorescent microparticles include additional dyes in or on the particles and/or bioreactive substances covalently bound or passively adsorbed to the surface of the microparticles.

DESCRIPTION OF THE DRAWINGS

FIG. 1: The relative fluorescence of polystyrene beads labeled with Compound 1 and coumarin 6. Spectra A) The emission spectrum of 1.09 micrometer polystyrene latex particles containing 50 mmol/gram of Compound 1 (see Table 1 below), excited at 490 nm (a preferred excitation wavelength). Spectra B) The emission spectrum of an identical concentration of identical latex particles containing 50 mmol/gram of coumarin 6, excited at 460 nm (excitation maximum).

FIG. 2: A comparison between a dipyrrometheneboron difluoride dye and another fluorescent dye relative to the consistency of the spectral response for the dyes in solvent and incorporated internally in the microparticles.

FIG. 3: The ability of multiple dipyrrometheneboron difluoride dyes to match the spectrum of a target material (Example 4).

FIG. 4: The response of indicator beads (as described in Example 5) to the effect of increasing concentrations of calcium ion.

DESCRIPTION OF PREFERRED EMBODIMENTS OF THE INVENTION

The novel fluorescent microparticles are prepared using derivatives of dipyrrometheneboron difluoride that are incorporated internally in polymeric microparticles. Typically, the dipyrrometheneboron difluoride dyes are derived from the dyes described in U.S. Pat. No. 4,774,339 (incorporated by reference) modified by substitution on either of the pyrrole rings or the non-boron linking group between these rings. Appropriate selection of substituents gives dipyrrometheneboron difluoride derivatives that, when incorporated into polymer particles, give desired excitation and emission wavelengths. Microparticles labeled by incorporation of dipyrrometheneboron difluoride dyes inside the microparticles retain the advantageous spectral properties of the dyes, such as the high extinction coefficient of the dyes (typically greater than 25,000 $cm^{-1}M^{-1}$, preferably greater than 50,000 $cm^{-1}M^{-1}$, more preferably greater than 70,000 $cm^{-1}M^{-1}$) and high quantum yield of the dyes (typically greater than 0.1, preferably greater than 0.2, more preferably greater than 0.5).

In one aspect of the invention, dipyrrometheneboron difluoride derivatives used for the preparation of fluorescent polymer microparticles according to this invention generally have the structure:

wherein $R^1$-$R^7$, which may be the same or different, are hydrogen, halogen, alkyl, alkoxy, aryl, arylalkyl, cycloalkyl, acyl, formyl, or cyano. Typically, $R^1$-$R^7$, which may be the same or different, are hydrogen, alkyl-, alkoxy-, aryl-, or halo-; and X is —$CR^4$=, where $R^4$ is hydrogen; or alkyl-, aryl-, or heteroaryl-substituted. More typically, $R^1$-$R^7$ are independently a hydrogen, hydrocarbon, or heteroaryl substituent.

Where microparticles with longer wavelength excitation and emission are desired, the dipyrrometheneboron difluoride derivatives used for the preparation of fluorescent polymer microparticles according to this invention generally have the structure described above, excepting that any or all of the substituents $R^1$-$R^7$, but at least one of such substituents, is an unsaturated organic group, i.e. a substituted or unsubstituted aryl, alkenyl, or heteroaryl group, or adjacent substituents $R^2$ and $R^3$ and/or $R^5$ and $R^6$ in combination form 1 or 2 fused unsaturated ring substituents, where each fused ring is optionally and independently substituted or unsubstituted. Dipyrrometheneboron difluoride dyes that are triazaindacene rather than diazaindacene dyes (where X is nitrogen) are equivalent to some diazaindacene dyes substituted with an unsaturated organic group in achieving desired red-shifting of microparticle emission spectra. Multiple unsaturated organic substituents, in combinations of $R^1$-$R^7$ may be the same or different. Generally, the remaining substituents are hydrogen, halogen, alkyl, alkoxy, arylalkyl, cycloalkyl, acyl, or formyl. Typically, remaining substituents are hydrogen or alkyl.

Incorporation of heteroaryl substituents results in dyes that have spectral properties that are significantly shifted from those of the parent alkyl-substituted fluorophore (excitation maxima, also emission maxima, typically exceed 540 nm; preferably the emission maximum exceeds 550 nm), thus permitting their use in multi-color fluorescence applications in combination with fluorescein or alkyl-substituted 4,4-difluoro-4-bora-3a,4a-diaza-s-indacenes. Furthermore, this wavelength shift is usually accompanied by an increase in photostability of the heteroaryl dyes and in some cases by an increase in the extinction coefficient of the heteroaryl dyes relative to the alkyl-substituted 4,4-difluoro-4-bora-3a,4a-diaza-s-indacenes (generally greater than 70,000 $cm^{-1}M^{-1}$).

In one embodiment, the heteroaryl group is a single ring structure containing one or more heteroatoms, for example, the heteroaryl substituent is pyrrole, thiophene, or furan (single ring, single heteroatom), or oxazole, isoxazole, oxadiazole, or imidazole (single ring, multiple heteroatoms). Alternatively, the heterdaryl group is a multi-ring structure containing one or more heteroatoms, for example, the heteroaryl substituent is benzoxazole, benzothiazole, or benzimidazole, (multi-ring, multiple heteroatoms), or benzofuran or indole (multi-ring, single heteroatom). The invention includes both heteroaryl substituents and substituted derivatives of the heteroaryl substituents, such as the preferred heteroaryl dyes where $R^1$ is pyrrolyl; or alkyl-, aryl-, arylalkyl- or heteroaryl-substituted pyrrolyl. In other preferred heteroaryl dyes, $R^1$ is thienyl; or alkyl-, aryl-, arylalkyl- or heteroaryl-substituted thienyl. In additional preferred embodiments of the heteroaryl dyes, $R^1$ and $R^7$, which may be the same or different, are pyrrolyl; or alkyl-, aryl-, arylalkyl- or heteroaryl-substituted pyrrolyl. Alternatively, $R^1$ and $R^7$, which may be the same or different, are thienyl; or alkyl-, aryl-, arylalkyl- or heteroaryl-substituted thienyl. Multiple heteroaryl substituents, in combinations of $R^1$-$R^7$ may be the same or different. In one embodiment, at least two of the substituents $R^1$-$R^7$, which may be the same or different, are heteroaryl residues.

Incorporation of alkenyl substituents likewise results in dipyrromethenboron difluoride dyes that are red-shifted and more photostable than the parent dyes. Typically, the alkenyl substituent is an ethenyl group that is directly coupled to the fluorophore through a single covalent bond, and is optionally substituted by hydrogen, halogen, alkyl (containing 1–10 carbon atoms), cyano, carboxylate ester, carboxamide, aryl or heteroaryl, or additional alkenyl groups to form a conjugated dienyl or trienyl substituent.

The fused ring substituents are fused benzo or heteroaromatic rings containing a total of 6 or fewer carbons, and 0, 1 or 2 heteroatoms selected from O, N, and S. Any benzo ring of the fused-ring-substituted dyes is optionally substituted or unsubstituted, as described in U.S. Ser. No. 08/246,790 by Kang, et al. filed May 20, 1994 (incorporated by reference). Each benzo substituent is optionally and independently substituted by an additional fused benzo or fused heteroaromatic ring, that is optionally further substituted. The substituents on the core structure or additional fused rings are selected from hydrogen, halogen, cyano, alkyl, perfluoroalkyl, cycloalkyl, alkoxy, alkylthio, substituted or unsubstituted aryl substituents, and substituted or unsubstituted heteroaryl substituents. All substituents have less than or equal to 25 carbon atoms. The benzo-substituted dipyrromethenboron difluoride dyes typically have an absorption maximum that is greater than 600 nm and an emission maximum that is greater than 650 nm but with various substituents can give an emission maximum that is greater than 700 nm.

Some aryl substituents also result in red-shifted dyes. Preferred aryl substituents are phenyl, 1-naphthyl, 2-naphthyl, 1-pyrenyl, 9-anthryl, and their alkyl, alkoxy and dialkylamino substituted derivatives. Aryl substituents are attached directly to the fluorophore, or are attached to the heteroaryl or alkenyl substituents on the fluorophore.

All alkyl portions of dye substituents, including alkyl, cycloalkyl, arylalkyl, acyl, and alkoxy substituents, generally contain fewer than 20 carbons, preferably fewer than about 10 carbons, often fewer than 5 carbons. Appropriate modification of alkyl substituents can also be used to affect the spectral properties and other physical properties of the dyes. The alkyl substituents are unsubstituted or substituted by H, halogen, cyano, amino, amido, hydroxy, or mercapto. Alkyl substituents are optionally attached to the core compound or to unsaturated organic substituents.

A wide-range of dipyrromethenboron difluoride dyes are commercially available under the trademark BODIPY (registered trademark of Molecular Probes, Inc., Eugene, Oreg.); and their synthesis is now well-documented in scientific and patent literature, including U.S. Pat. No. 4,774,339 to Haugland, et al. (1988); U.S. Pat. No. 4,916,711 to Boyer, et al. (1990); U.S. Pat. No. 5,187,288 to Kang et al. (1993); U.S. Pat. No. 5,248,782 to Haugland, et al. (1993); U.S. Pat. No. 5,274,113 to Kang, et al. (1993); U.S. Pat. No. 5,326,692 to Brinkley, et al. (1994); U.S. Pat. No. 5,338,854 to Kang, et al. (1994); and in U.S. Ser. No. 08/246,790 by Kang, et al. filed May 20, 1994, all incorporated by reference.

These novel fluorescent microparticles have fluorescence emission wavelength similar to fluorescein, rhodamine B, rhodamine 6G, sulforhodamine 101, oxazine 170, 3,3'-diethylthiadicarbocyanine, 3,3'-diethyloxatricarbocyanine, and Cy5. For example, when $R^1$, $R^2$, $R^3$, $R^4$, and $R^6$ are hydrogen, and $R^5$ and $R^7$ are methyl, the particles have yellow-green fluorescence emission centered at about 512 nm. When $R^1$ and $R^3$ are methyl, $R^2$, $R^4$, and $R^6$ are hydrogen, and $R^5$ and $R^7$ are phenyl, the particles have orange fluorescence emission centered at about 560 nm. When $R^1$, $R^3$, $R^5$ and $R^7$ are phenyl and $R^2$, $R^4$, and $R^6$ are hydrogen, the particles have red fluorescence emission centered at about 605 nm. When $R^1$ and $R^3$ are phenyl, $R^7$ is pyrrol-2-yl and $R^2$, $R^4$, $R^5$ and $R^6$ are hydrogen, the particles have a dark red fluorescence emission centered at about 645 nm. As a result, the microparticles can be detected and analyzed by instruments designed to be sensitive to emission wavelengths of those dyes. For example, the microparticles' emission wavelengths of about 515, 560 and 605 nm are compatible with commonly used filters for fluorescein, rhodamine and TEXAS RED (registered trademark of Molecular Probes, Inc., Eugene Oreg.) dyes.

TABLE 1

Dipyrromethenboron Difluoride Dyes* Used for Fluorescent Microparticles

| Compound | $R^1$ | $R^2$ | $R^3$ | $R^4$ | $R^5$ | $R^6$ | $R^7$ |
|---|---|---|---|---|---|---|---|
| 1 | H | H | H | H | $CH_3$ | H | $CH_3$ |
| 2 | $CH_3$ | H | $CH_3$ | H | $CH_3$ | H | $CH_3$ |
| 3 | $CH_3$ | H | $CH_3$ | H | Ph | H | Ph |
| 4 | Ph | H | Ph | H | Ph | H | Ph |
| 5 | Ph | H | Ph | H | H | H | Pyr† |
| 6 | Ph | H | Ph | n/a* | Ph | H | Ph |
| 7 | $CH_3$ | $C_2H_5$ | $CH_3$ | $CH_3$ | $CH_3$ | H | $CH_3$ |
| 8 | $CH_3$ | H | $CH_3$ | $CH_3$ | $CH_3$ | H | $CH_3$ |
| 9 | H | H | H | H | $C_3H_7$ | H | $C_3H_7$ |
| 10 | PhBD† | H | H | H | H | H | PhBD† |

*Representative examples, non-exclusive; for compound 6, X is N, and there is no $R_4$; for all other compounds, X is —$CR_4$=
†Pyr is pyrrol-2-yl; PhBD is —CH=CH—CH=CH—Ph

TABLE 2

Spectral Data for Dyes in Table 1

| Compound | $\lambda^{Abs}_{max}$ (nm)† | $\lambda^{Em}_{max}$ (nm)† | $\lambda^{Abs}_{max}$ (nm)‡ | $\lambda^{Em}_{max}$ (nm)‡ |
|---|---|---|---|---|
| 1 | 490 | 503 | NA | NA |
| 2 | 505 | 515 | 504 | 512 |
| 3 | 528 | 548 | 540 | 557 |
| 4 | 564 | 591 | 578 | 605 |
| 5 | 606 | 633 | 625 | 645 |
| 6 | 644 | 668 | 650 | 679 |
| 7 | 503 | 519 | 509 | 525 |

TABLE 2-continued

Spectral Data for Dyes in Table 1

| Compound | $\lambda^{Abs}_{max}$ (nm)† | $\lambda^{Em}_{max}$ (nm)† | $\lambda^{Abs}_{max}$ (nm)‡ | $\lambda^{Em}_{max}$ (nm)‡ |
|---|---|---|---|---|
| 8 | 491 | 503 | 494 | 506 |
| 9 | 490 | 503 | 499 | 513 |
| 10 | 665 | 676 | 672 | 685 |

†Absorption maxima ($\lambda^{Abs}_{max}$) and emission maxima ($\lambda^{Em}_{max}$) measurements of free dye in methanol.
‡Absorption maxima ($\lambda^{Abs}_{max}$) and emission maxima ($\lambda^{Em}_{max}$) measurements of dye in aqueous suspension of latex.
Optical density set at 0.1 at 700 nm.

Figure 1:
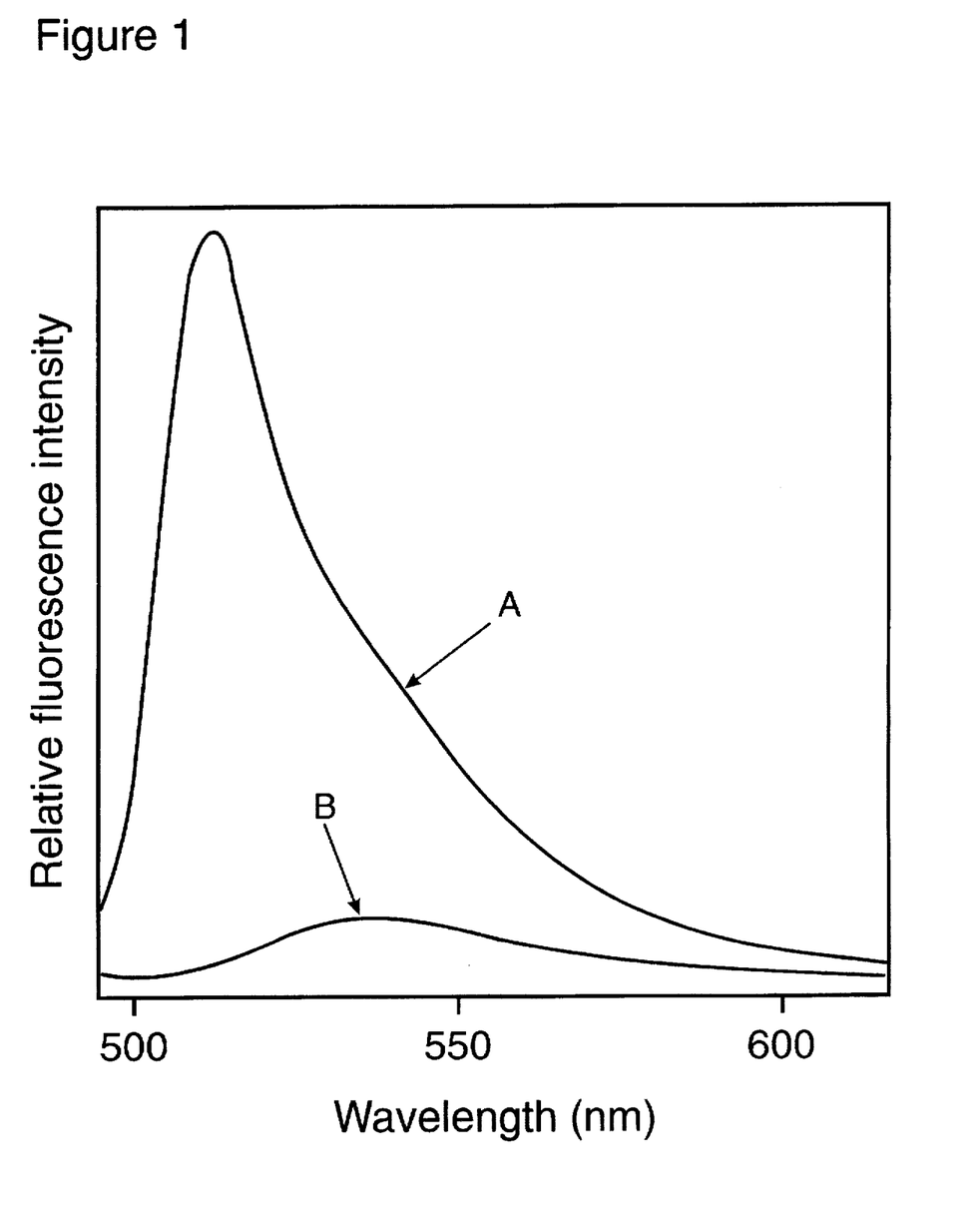

The subject microparticles have superior fluorescence efficiency (quantum yield) compared to microparticles prepared with other dyes such as coumarin 6. For example, comparison of 1.09 micrometer polystyrene particles labeled with Compound 1 and 1.09 micrometer particles labeled with coumarin 6 shows that the Compound 1—labeled particles have many times greater fluorescence (see FIG. 1). Comparison of the beads of this invention with a number of commercially available fluorescent beads labeled with undisclosed dyes other than those of the invention, shows the superior fluorescence of beads labeled with dipyrrometheneboron difluoride dyes. (see Example 3, Table 3).

The subject microparticles have superior photostability compared to microparticles containing other dyes such as fluorescein. For example, 5.17 micrometer particles labeled with Compound 1 were not visibly photobleached under illumination with a fluorescent microscope excitation source for 30 minutes, while under the same illumination conditions, fluorescein-labeled 5.8 micrometer particles were almost completely photobleached within 2 minutes. This superior fluorescence efficiency and photostability is especially important in development of immunodiagnostic tests, since increased fluorescence intensity translates to increased sensitivity of the test.

Figure 2A:
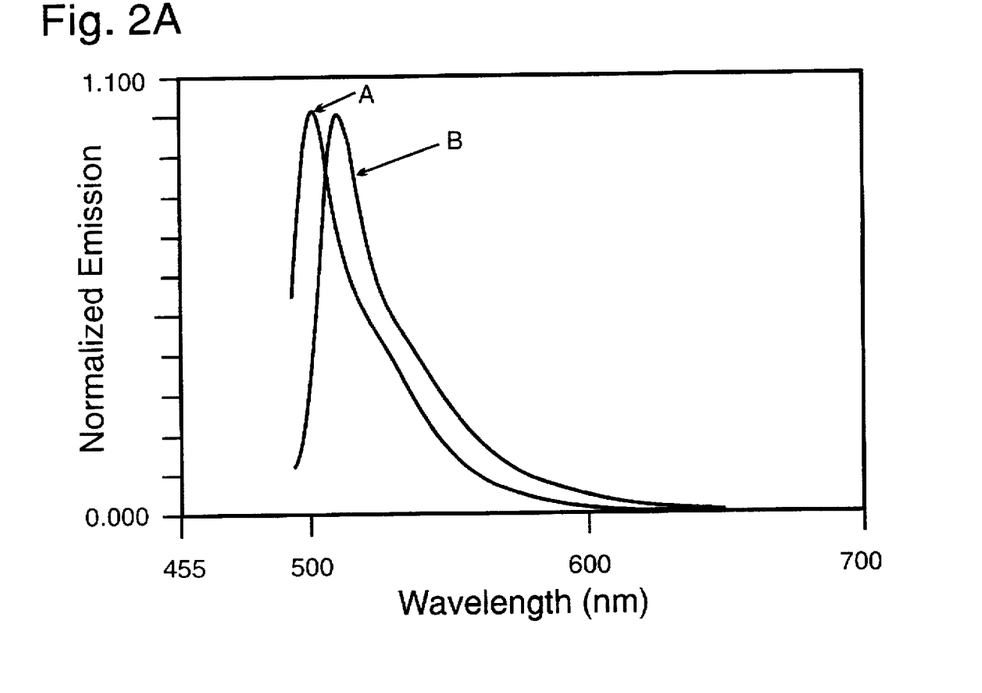
FIG. 2A shows the normalized emission spectra of Compound 1 in methanol solution (spectrum A) and incorporated into 30 nm polystyrene microparticles (spectrum B).
Figure 2B:
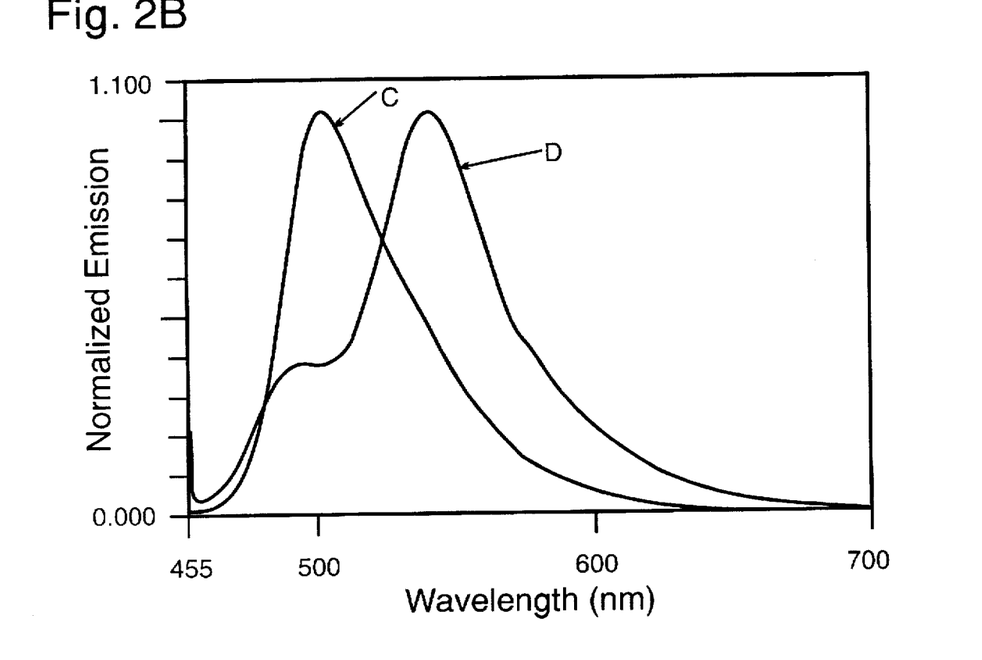
FIG. 2B shows the normalized emission spectra of coumarin 6 in methanol solution (spectrum C) and incorporated into 30 nm polystyrene microparticles (spectrum D). Each set of spectra are plotted against the same x-axis scale, from 455 to 700 nm. Since the spectra in FIGS. 2A and 2B are normalized (i.e. adjusted to the same peak height) for ease of comparison, the peak height in FIGS. 2A and 2B is not indicative of relative fluorescence intensity for either compound in solvent or after incorporation into the microparticles. The spectrum of Compound 1 shifts very little upon incorporation into the microparticle. In contrast, the very broad emission of coumarin 6 shifts in both emission wavelength and bandshape upon being incorporated into the microparticle, and becomes even broader.

Unlike many other fluorescent dyes, the spectral properties of dipyrrometheneboron difluoride dyes are not substantially altered by their inclusion into the solid phase of the polymer microparticles, i.e., their excitation and emission maxima and Stokes shift are similar to that observed in the solution phase (see FIG. 2). This property facilitates the preparation of microparticles with spectra and intensity selected to match those of other materials, including those of biological materials such as cells and fluorescent proteins (see FIG. 3). The labeled microparticles can be excited by either incandescent or laser-based excitation sources.

In one aspect of the invention, a mixture of 2–7 dipyrrometheneboron difluoride dyes is internally incorporated, simultaneously or sequentially, into the polymeric microparticles to give the microparticles spectral characteristics that closely resemble the spectral characteristics of both intensity and wavelength distribution of a target material (Example 4). Preferably the dyes are incorporated into the microparticles to an internal total dye concentration at which minimal dye-dye interactions occur, typically below 1–3 mM internal total dye concentration. Internal dye concentration depends on a number of factors, including differing dye hydrophobicity, differing dye uptake rates, differing solvent-induced swelling of microparticles, and is difficult to determine. In general, however, a dye concentration for each dye that is less than 50% of the concentration needed to achieve the saturating intensity for the same dye, in the same polymeric microparticle, in a given solvent will be below the dye-dye interaction distance. Where more than two dyes are used, this is typically less than 20% of the dye needed for the saturating intensity, more typically less than 10% of the dye needed for the saturating intensity, depending on the number of different dyes incorporated into the microparticles. Saturating intensity as used in this document means the substantially maximum fluorescence intensity achieved with a minimal amount of dye, whereby further increases in the dye amount have minimal effect on increasing the intensity and may, in fact, decrease intensity due to dye-dye quenching.

The following characteristics of the dipyrrometheneboron difluoride dyes are important when matching the spectral characteristics of a target material: 1) the spectral profile of the individual dyes in solvent changes little upon incorporation into the microparticle (typically less than 5–10 nm shift at the emission maximum); 2) there is a substantially linear relationship between dye concentration and intensity when the concentrations are below the dye-dye interaction distance; 3) the narrow spectra of the dyes facilitate more precise spectral tuning with the dye mixtures; 4) the dyes are sufficiently fluorescent to still give a useful signal at the low concentrations needed to avoid most dye-dye interactions. In determining the proportion of each of the dyes to be used to match the emission spectra of the target material, the intensity values for the spectral profiles of each of the dyes (at standard concentrations) are determined in solution at a target excitation wavelength desired to be used with the target material. The intensity values for each spectral profile are added together to get a composite spectral emission profile, and the relative proportions of each of the dyes are adjusted to give a composite spectral emission substantially similar to that of the target material. The addition of spectral profiles and the adjustment of relative proportions to get a close match is readily simulated on a computer (starting with the standard experimental values determined in the previous step), and these proportions are optionally adjusted in practice to optimize the match.

The mixture of dyes, and the relative proportion of dyes in such mixture, is selected for incorporation into a microparticle such that microparticle has an emission wavelength distribution curve in a given solvent that substantially matches that of the target material in the same solvent, when illuminated at the target excitation wavelength. The emission wavelength distribution curve "substantially matches" that of the target material when the intensity at any emission wavelength deviates less than 10% (preferably less than about 5%) from the intensity of the corresponding emission wavelength of the target material between the range of 15% of peak intensity and the peak intensity (i.e. the upper portion of the spectral peak above 15% of peak intensity), provided that the emission peaks are normalized to the same intensity. Preferably the emission maximum of the microparticle is also within 5 nm, more preferably within 2 nm, of the emission maximum of the target material. It is also preferable that the spectral width at half height of the emission wavelength distribution curve of the microparticle is within 5% of that of the target material. Preferably illumination of the microparticles is accomplished with a near monochromatic excitation (e.g. laser or narrow band filter at the target excitation wavelength used with a broad band source), and may be less effective under variations of broad band excitation because of the heterogeneity of the excitation profiles in the mixture.

The target material matched using the beads of the invention is typically a material containing a fluorescent dye or dyes, such as a cell, solution, or solid material (e.g. a microparticle or other polymer or plastic material). Typically the target material comprises one or more fluorescent dyes that is a fluorescein, a rhodamine, a carbocyanine (such as Cy 3 or Cy 5 described in U.S. Pat. No. 5,268,486 to Waggoner, et al. (1993), incorporated by reference), a nucleic acid stain (e.g. a phenanthridine such as ethidium or propidium, or an unsymmetrical cyanine dye as described in U.S. Pat. Nos. 5,410,030 or 5,321,130 to Yue, et al., or in WO 93/06482 published Apr. 1, 1993 or WO 94/24213 published Oct. 27, 1994, all incorporated by reference) or a natural pigment (e.g. an expressed transfected protein such as green fluorescent protein (GFP), or a phycobiliprotein such as R-phycoerythrin or allophycocyanin, or peridinin-chlorophyll a-protein). In one aspect of the invention, a mixture of dyes is incorporated into microparticles approximating the size of target cells (typically 6 μm), where the mixture is selected to match the spectral characteristics of the stained target cell. In another aspect of the invention, two dyes are incorporated into microparticles with a spectrum substantially matching that of conjugates of fluorescein in pH 8 buffer or R-phycoerythrin, sulforhodamine 101, or Cy 5 in water.

A major improvement of the subject microparticles is that the oil-soluble fluorescent dipyrromethaneboron difluoride dyes, being freely soluble in organic solvents and very sparingly soluble in water, can easily be introduced by solvent-based addition of the dye to previously manufactured polymer microparticles, which offers the great advantage of being able to prepare uniform polymer microparticles with desired properties by carefully optimized procedures (which may not necessarily be compatible with dye incorporation by stock dying methods) and then later adding the fluorescent dye of choice. In this manner, large batches of uniformly-stained microparticles with desired physical properties, such as size and charge density, can be prepared. Then the various fluorescent dipyrromethaneboron difluoride dyes can be added to smaller portions of this product to give fluorescent polymer microparticles with consistent and reproducible performance in applications such as development of diagnostic tests. Where additional dipyrromethaneboron difluoride dyes are incorporated into the microparticles from an organic solvent, the dyes are added simultaneously or sequentially, according to ratios selected to give desired combinations of spectral properties. In the case of fluorescent microparticles prepared by solvent-based addition of the dye to previously manufactured polymer microparticles, the surface properties of the subject fluorescent microparticles are not substantially different from the surface properties of the corresponding undyed microparticles. The labeled microparticles are also not affected by changes in pH.

Furthermore, the dyes used in the subject microparticles are not significantly removed from the microparticles by the water-based solvents that are commonly used as a suspension medium for the microparticles. For example, when aqueous suspensions of fluorescent microparticles containing Compound 4 (Table 1) were subjected to temperatures of 60° C. in the presence of 0.2% sodium dodecyl sulfate, no detectable dye was extracted from the particles. When carefully prepared, the subject fluorescent microparticles are monodisperse in aqueous suspension, as determined by fluorescence microscopy or flow cytometry. For example, 1.09 micrometer polystyrene microspheres dyed with Compound 1 were shown to be monodisperse by both visual observation (epifluorescence microscopy) and flow cytometric analysis. Flow cytometric analysis, where the coefficient of variation of size was found to be 6.27% and the coefficient of variation of fluorescence was found to be 5.27%, also indicates uniformity of labeling.

The polymer microparticles are prepared from a variety of suitable compositions including, but not limited to, glass, and polymers of styrene, bromostyrene, acrylic acid, acrylonitrile, acrylamide, methyl methacrylate, vinyl chloride, vinyl benzyl chloride, vinyl acetate, vinyl toluene, vinyl pyridine, vinylidene chloride, divinyl benzene, butadiene, isoprene, and urethane. The microparticles are spherical or irregular in shape, and between about 0.01 and about 50 micrometers in diameter; preferably less than 50 micrometers in diameter. Typically, the labeled microparticles are spherical and between about 0.01 and about 15 micrometers in diameter. Where bioreactive materials or additional dyes are attached to the external surface of the microparticles, such microparticles (usually spherical) are typically 5 micrometers or less in diameter; the smaller the bead, the greater the proportion of surface material relative to the amount of fluorescent dye incorporated in the interior of the microparticle. The microparticles may be of uniform size and/or shape or non-uniform.

The subject fluorescent microparticles can be prepared with a variety of surface properties, with functional groups including, but not limited to sulfate, phosphate, hydroxyl, carboxyl, ester, amide, amidine, amine, sulfhydryl and aldehyde. Surface groups are important for use in covalent binding of additional substances to the surface of the microparticles. The surface groups can also be selected to give the particles desired physical characteristics such as varying degrees of hydrophilicity. The surface properties can be added by any methods known in the art. Bangs, UNIFORM LATEX PARTICLES Ch. VII (1984 Seragen, Inc.), incorporated herein by reference, describes methods of attaching such groups to microparticles. The microparticles optionally include components that alter other physical properties (e.g. magnetic, radioactive, or gold-plated beads).

The fluorescent dye is incorporated into the microparticles by any one of a variety of suitable methods known in the art. The method of incorporating the dye, as well as the method used to attach additional dyes, surface functional groups, and/or bioreactive substances will depend on a number of factors, including the desired characteristics of the microparticles, the contemplated method and environment of use of the microparticles, economic considerations, availability of certain materials, etc. The fluorescent dyes are incorporated into the microparticles by any of the methods known in the art, including without limitation a) copolymerization of a monomer and a dye-containing comonomer, b) addition of a suitable dye derivative in a suitable organic solvent to an aqueous suspension of polymer microparticles, and c) chemical reaction of a suitable dye derivative with microparticle surface groups.

For example, the fluorescent microparticles can be produced by free radical-initiated, anaerobic copolymerization of an aqueous suspension of a mono-unsaturated monomer that may or may not contain a covalent bonding group such as carboxyl, amino or hydroxyl and a fluorescent dipyrromethaneboron difluoride dyes monomer mixture containing at least 10% by weight of monomers, according to the method of Rembaum (U.S. Pat. No. 4,326,008 (1982)) the disclosure of which is incorporated herein by reference. The fluorescent microparticles can also be produced by gradual addition of a solution of an appropriate fluorescent dipyrromethaneboron difluoride dyes in an appropriate solvent to a stirred aqueous suspension of microparticles to incorporate the dye internally without covalent attachment, according to Example 1, below, or as described by Bangs, pp. 40–42. The fluorescent microparticles can also be produced by addition of an activated derivative of a selected fluorescent dipyrrometheneboron difluoride dye compound to an aqueous suspension of microparticles that have surface functional groups capable of forming a covalent bond with the activated dye molecules. Such methods are known in the art and are described in the following three U.S. patents, the disclosures of which are incorporated by reference: U.S. Pat. No. 3,857,931 to Hager (1974); U.S. Pat. No. 4,046,723 to Dorman (1977); U.S. Pat. No. 4,421,896 to Dorman (1983); and in Bangs. The modification of dipyrrometheneboron difluoride dyes to include chemically reactive functional groups for attachment to polymers is described in U.S. Pat. No. 4,774,339 to Haugland, et al. (1988); U.S. Pat. No. 4,916,711 to Boyer, et al. (1990); U.S. Pat. No. 5,187,288 to Kang et al. (1993); U.S. Pat. No. 5,274,113 to Kang, et al. (1993); and U.S. Ser. No. 08/246,790 by Kang, et al. filed May 20, 1994, (all incorporated by reference).

The fluorescent dipyrrometheneboron difluoride dyes compounds that are used to prepare the subject fluorescent polymer microparticles are lipophilic and electrically neutral, and therefore do not contribute to or alter the charged properties of the polymer microparticles as do other fluorescent dyes such as fluorescein and rhodamine 6G, that are commonly used to prepare fluorescent microparticles. As a result, the subject fluorescent microparticles can also include a variety of other substances in addition to dipyrrometheneboron difluoride dyes, such as other fluorescent and/or non-fluorescent dyes. The additional dyes can be added by the same methods used in the manufacture of the labeled microparticles; i.e. by simultaneous or sequential addition using, for example, the method described in Example 1, below, or through use of multiple reactive dyes either simultaneously or sequentially, or through copolymerization of multiple dyes that contain the required reactive functions.

The microparticles optionally include bioreactive substances. Bioreactive substances are substances that react with or bind to molecules that are derived from a biological system, whether such molecules are naturally occurring or result from some external disturbance of the system (e.g. disease, poisoning, genetic manipulation). By way of illustration, bioreactive substances include biomolecules, i.e. molecules of biological origin including, without limitation, peptides; proteins (such as polyclonal and monoclonal antibodies, enzymes, avidin, streptavidin, protein A, and protein G); nucleic acid compounds such as nucleotides, oligonucleotides, DNA and RNA; and non-polymeric biomolecules such as biotin and digoxin. Bioreactive substances also include carbohydrates such as lectin and polysaccharides; microscopic organisms such as viruses; toxins; and haptens including hormones, vitamins, and drugs.

The additional bioreactive substances are attached to the surface of the microparticles by methods known in the art. Generally the bioreactive substances are either covalently attached (for example, following the procedure in Example 2, below, or as described in Guilford, *Chemical Aspects of Affinity Chromatography*, CHEM. SOC. REV. 2: 249 (1973) incorporated herein by reference) or non-covalently adsorbed (for example, by methods described in Nathan & Cohn, *Antitumor Effects of Hydrogen Peroxide in Vivo*, J. EXP. MED. 154:1539 (1981), incorporated herein by reference) to the surface of the microparticles (see also U.S. Pat. No. 4,326,008 to Rembaum (1982) (for microparticles containing amine surface functional groups); and Bangs, pp. 31–40). These surface-attached or adsorbed molecules are best added to the microparticles after the fluorescent dyes have been incorporated. These modifications make the subject microparticles useful in a wide variety of diagnostic tests.

In one embodiment of the invention, the microparticles are interconnected by bridging two or more particles by means of a bi- or multivalent ligand, such as an antibody. The bridging is accomplished by known methods, such as methods described in Bangs, supra, pp. 51–58. This bridging creates larger particles which can be detected and serves as a method for identifying and quantitating antibodies and other molecules of interest. In this way, particles to which antigens are attached are used to identify and quantitate antibodies to these antigens.

In one aspect of the invention, the dipyrrometheneboron difluoride dyes are incorporated internally into the microparticles, typically without covalent attachment by absorption of the dyes in an organic solvent. One or more different dyes are then covalently attached to the surface of the microparticle, either directly or through an organic linker or spacer. The external dye(s) are typically fluorescent or colorimetric. Typically, where the external dye is fluorescent, the external and internal dyes are excited with the same wavelengths, and the emission is measured at two wavelengths, one of which is the primary emission wavelength of the internal dye and the other of which is the primary emission wavelength of the external dye. Alternatively, the microparticle is dual excited—at optimal wavelengths for each dye, or is synchronously scanned for excitation and emission wavelengths (Example 5). It is not generally necessary that the dye inside the microparticle absorbs well at the excitation wavelength of the external dye because there is generally so much more dye inside the microparticle than there is external dye on the surface.

External attachment of dyes to the microparticle using a hydrophilic polymer facilitates the projection of the dyes away from the surface of the microparticle and into the surrounding environment. Appropriate hydrophilic polymers include polysaccharides (e.g. dextran), poly (ethyleneglycol), and proteins or other amino acid polymers (e.g. bovine serum albumin (BSA)). The hydrophilic polymer typically has an average molecular weight between 5000 and 500,000 Daltons, preferably the average molecular weight of the polymer is between about 50,000 and 100,000 Daltons. Using a molar ratio of about 15:1 for dye to polymer, the external dyes are generally first attached to the polymer, with sufficient reactive attachment sites remaining on the polymer to attach the labeled polymer to the bead, where the bead has been modified to contain reactive functional groups, e.g. amino or carboxylate modified beads, as in Example 5 where about half the reactive sites on the polymer are attached to dye molecules, and the remainder are free for coupling the dyed polymer to the bead. The amount of hydrophilic polymer needed depends on a number of factors well known in the art, including the size of the bead, the distribution of labeling desired, the reactivity of the polymer, the amount of dye to be attached, etc.

In one aspect of the invention, one eternally conjugated dye is used to detect the presence of an analyte in the environment surrounding the microparticle by means of a detectable response as a result of the presence of that analyte. A detectable response means a change in, or occurrence of, a parameter in a test system that is capable of being perceived, either by direct observation or instrumentally, and which is a function of the presence of a specifically targeted member of a specific binding pair in a sample. Such detectable responses include the change in, or appearance of, color, fluorescence, reflectance, pH, chemiluminescence, infrared spectra, magnetic properties, radioactivity, light scattering, or x-ray scattering. Appropriate labels to provide a detectable response include, but are not limited to, a visible or fluorescent dye, an enzyme substrate that produces a visible or fluorescent precipitate upon enzyme action (e.g., U.S. Pat. No. 5,316,906 to Haugland, et al. (1994) incorporated by reference) or a signal that is released by the action of light upon the reagent (e.g. a caged fluorophore that is activated by photolysis, or the action of light upon diaminobenzidine). Typically the detectable response is a change in fluorescence, such as a change in the intensity, excitation or emission wavelength distribution of fluorescence or a combination thereof.

In one embodiment of the invention, one external fluorescent dye is an indicator of the pH in the microparticle surroundings. A number of fluorescent, chemically reactive, pH indicator dyes can be used to prepare such indicating microparticles, including BCECF, fluorescein, and rhodol dyes described in U.S. Pat. No. 4,945,171 to Haugland, et al. (1990) (incorporated by reference) sold under the trademark SNARF (registered trademark of Molecular Probes Inc., Eugene Oreg.) and rhodol dyes described in U.S. Pat. No. 5,227,487 to Haugland, et al. (1993) (incorporated by reference).

Figure 4A:
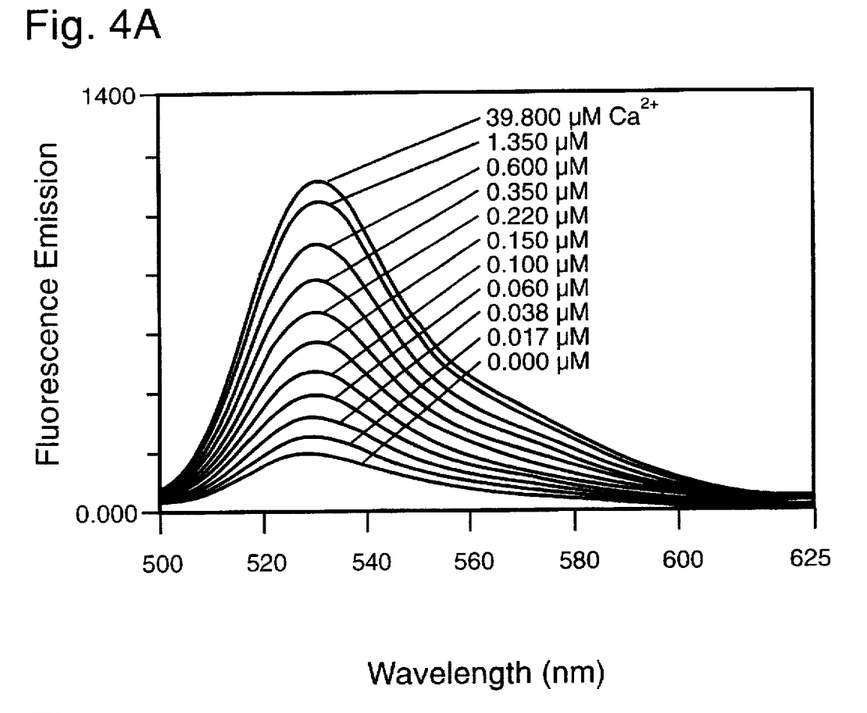
FIG. 4A shows the fluorescence emission response of 14 nm microparticles labeled with a non-ratioable calcium ion indicator. The dissociation constant, Kd, of the indicator is 205 nM, within the physiological $Ca^{2+}$ range.

In another embodiment, one external dye is a fluorescent indicator of calcium, sodium, magnesium, potassium, or other biologically important metal ion. A number of fluorescent, chemically reactive, metal ion indicators are useful in the preparation of such microparticles, including fluorescent crown ether conjugates such as described in UK application 9406231.2 (U.S. Ser. No. 08/038,918 by Kuhn, et al. filed Mar. 29, 1993) (incorporated by reference), e.g. sold under the trademark SODIUM GREEN (registered trademark of Molecular Probes, Eugene Oreg.); fluorescent reactive BAPTA conjugates such as described in U.S. Ser. No. 07/843,360 by Kuhn, et al. filed Feb. 25, 1992 (incorporated by reference), e.g. sold under the trademarks CALCIUM GREEN, CALCIUM ORANGE, and CALCIUM CRIMSON (trademarks of Molecular Probes, Eugene Oreg.); and fluorescent conjugates of nitrogen heterocycles for chelating heavy metals such as described in U.S. Ser. No. 08/384,945 by Kuhn, et al. filed Feb. 6, 1995 (incorporated by reference), e.g. sold under the trademarks NICKEL GREEN and PHEN GREEN (trademarks of Molecular Probes, Eugene, Oreg.); benzazolylcoumarin-based ion indicators described in U.S. Ser. No. 08/246,847 by Kuhn, et al. and Ser. No. 08/247,013 by Katerinopoulos, et al., both filed May 20, 1994 (both incorporated by reference), e.g. sold under the name BTC and BTC5N. Use of these double-labeled microparticles allows the researcher to overcome the disadvantage of nonratioable indicators and obtain a ratioable metal ion or $H^+$ ion concentration (see FIG. 4), or to shift the wavelengths at which the response for an indicator is measured, or to make any indicator into a dual emission indicator.

In yet another embodiment of the invention, one external dye is an enzyme substrate. A number of enzyme substrates, including substrates for glucosidase, peroxidase and phosphatase enzymes (e.g. dihydrofluoresceins and fluorescein digalactoside), can be attached to the fluorescent microparticles by means generally known in the art. The fluorescence of the product formed by metabolism of the substrate can be ratioed to fluorescence of the internally incorporated dye, thus providing a built in reference standard.

The following illustrations describe the practice of the invention and are by way of example and not by way of limitation.

EXAMPLES

Example 1

Preparation of Red Fluorescent Polystyrene Microspheres

To a vigorously stirred 100 mL suspension of 0.28 micrometer carboxylate-modified latex microspheres (Interfacial Dynamics Corp., Portland, Oreg.) (5.4% solids in distilled water) is added 3.75 mL of a solution of 25 mg of Compound 4 in dichloromethane. The addition of the dye is carried out by means of a syringe pump fitted with a TEFLON delivery tube (0.038 ini.d.) and the dye solution is delivered at such a rate that each drop of the solvent/dye solution is absorbed as completely as possible before the next drop is delivered. Typically, a 30 mL glass syringe is used and the rate of addition is 0.4 mL/hr. After addition is complete, the suspension is filtered through loosely packed glass wool to remove any debris and then partially evaporated at room temperature on a rotary evaporator to remove the dichloromethane. The aqueous suspension of dyed latex is then filtered again through glass wool to remove any additional debris and dialyzed (25 mm tubing, MW cutoff 12,000–14,000) to remove any residual dye. The dialysis is carried out until no more free dye is removed from the particles as detected by fluorimetric analysis of the dialysate. The fluorescent latex suspension is removed from dialysis and filtered again through glass wool to remove any remaining aggregates and other debris. The suspension is then sonicated in a bath sonicator for 10 minutes to ensure monodispersity. Visual analysis of a dilute aqueous suspension of the product by fluorescence microscopy using standard fluorescein filters show uniformly dyed particles that are highly monodisperse.

Example 2

Coupling of Red Fluorescent Polystyrene Latex Microspheres to Avidin

To a 5 mL suspension of 0.28 micrometer red fluorescent latex microspheres (prepared as above) (2% suspension in distilled water) in a 15 mL glass centrifuge tube is added 2 mL of 15 mM pH 5.0 2-(N-morpholino)ethanesulfonic acid, sodium salt (MES), 4 mg of avidin and 40 mg of (1-ethyl 3-(3-dimethylaminopropyl)-carbodimide). The contents of the tube are mixed by vortexing for approximately one minute and then the mixture is incubated on a rocker or orbital shaker for two hours at room temperature. The particles are separated from the suspending medium by centrifugation at 6000 rpm for 30 minutes. The supernatant fluid is decanted and the particles are re-suspended in 5 mL of 50 mM pH 7.4 phosphate buffered saline (PBS) containing 1% bovine serum albumin and centrifuged again. The microspheres are washed an additional three times by centrifugation with 50 mM PBS, pH 7.4 and re-suspended the final time in 5 mL of this buffer. The microspheres are shown to bind to a protein A-biotin conjugate by a dot-blot test.

Example 3

Comparison of Fluorescence Intensity of Commercially Available Fluorescent Microbeads Samples of microbeads with yellow-green fluorescence were obtained from commercial suppliers. Two sizes of polystyrene beads (Bead A, Bead B) were labeled with Compound 9, according to Example 1. The fluorescence intensity was measured for all beads using flow cytometer analysis (FACScan, Becton Dickinson, San Jose, Calif.); 10,000 events (individual beads) were measured from each sample. The data are summarized in Table 3.

TABLE 3

Flow Cytometry Analysis of Selected Yellow-Green Fluorescent Microparticles

| Supplier | Cat. No. | Size (μm) | Fluorescence* (Excitation 488 nm Emission 515 nm) | Coefficient of Variation in intensity |
|---|---|---|---|---|
| Spherotech | FP-0852-2 | 0.85 | 17 | 5.19% |
| Spherotech | FH2052-2 | 1.84 | 119 | 3.08% |
| Bangs Lab | L930216D | 0.84 | 3.7 | 30.28% |
| Bangs Lab | L900215H | 1.55 | 5.2 | 11.69% |
| Polysciences | 15702 | 0.93 | 116 | 4.62% |
| Polysciences | 09719 | 1.48 | 434 | 1.92% |
| Duke Scientific | G0100 | 1.01 | 12.6 | 2.49% |
| Duke Scientific | G0190 | 1.94 | 595 | 2.91% |
| Bead A | | 1.02 | 1998 | 4.40% |
| Bead B | | 2.07 | 8998 | 3.26% |

*Median value.

Even the smaller of the two beads labeled with dipyrrometheneboron difluoride dyes (Bead A) was significantly more fluorescent than the other beads tested.

Example 4

Matching Spectral Characteristics of Target Material

Figure 3A:
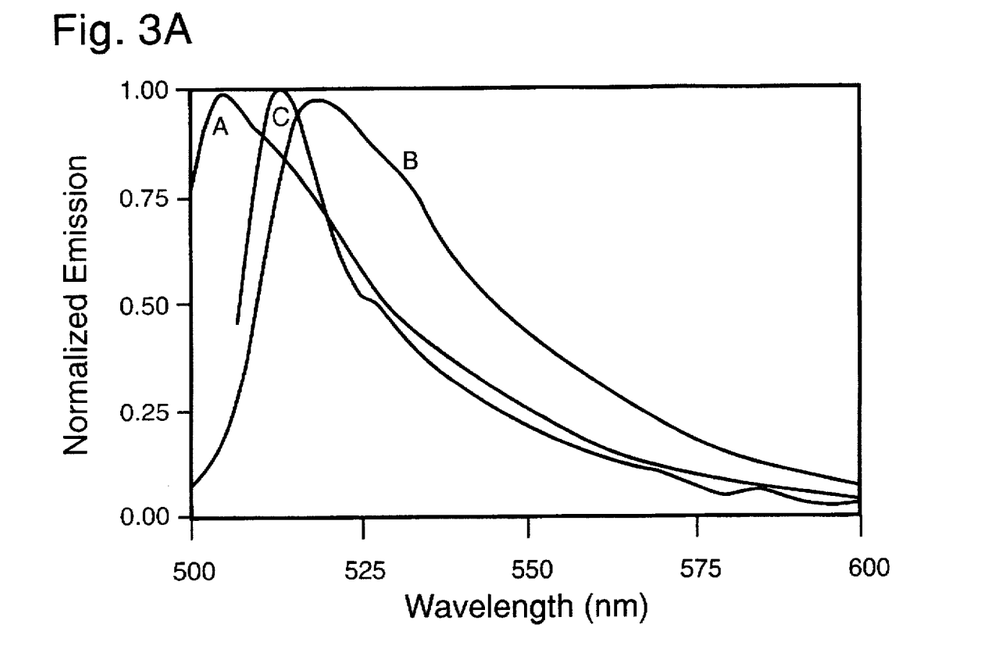
FIG. 3A shows the spectra of microparticles I and II, each labeled with a different dipyrrometheneboron difluoride dye (spectra A and B, respectively), in comparison with the spectrum of the target material: a bead surface-labeled with fluorescein isothiocyanate ("FITC bead", spectrum C).

Stock solutions of compounds 7 and 8 are prepared from 0.02 mg/mL dye in organic solvent (10% $CH_2Cl_2$ in 30% MeOH, 70% EtOH). 1 mL of 10% 5.1 μm polystyrene beads (Bangs, Indianapolis, Ind.) in 4 mL MeOH are divided into two equal portions I and II. Each portion is washed with MeOH. While stirring, 1 mL of stock solution of compound 8 is added to portion I and 1 mL of stock solution of compound 7 is added to portion II. After stirring for 90 minutes at room temperature, beads are spun down and excess dye is removed. After washing with MeOH three times, then with 0.02% Tween 20 in water three times, beads are suspended in 0.02% Tween 20 in water, $As_{800}$=2.0. Spectra for microparticles from portion I and portion II, excited at 488 nm, scattering corrected, are shown in FIG. 3A.

Figure 3B:
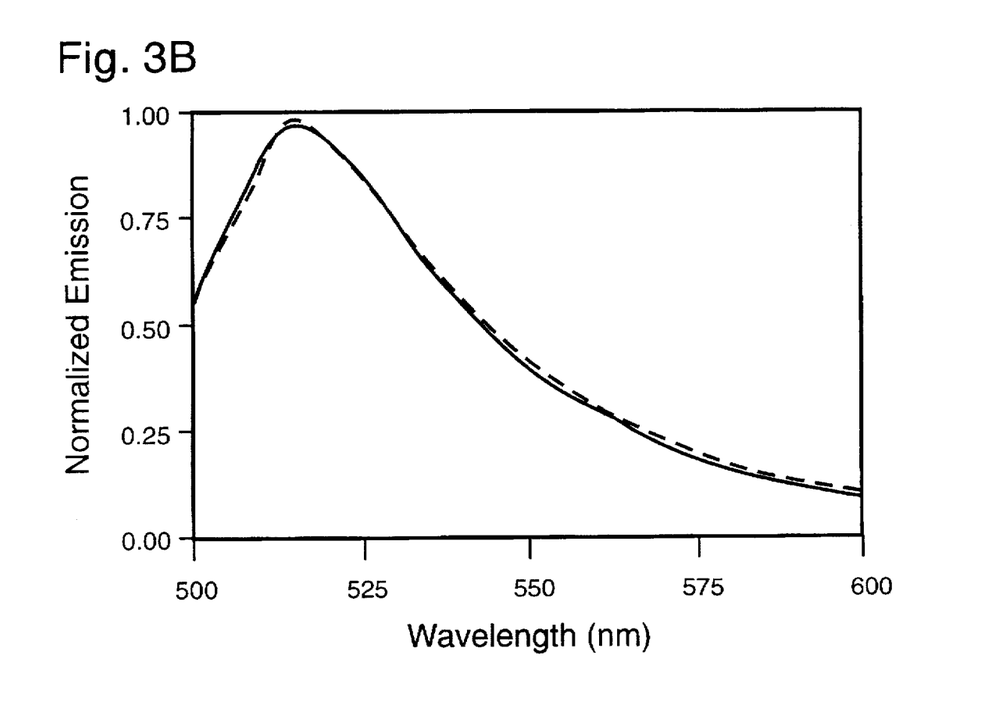
FIG. 3B shows the spectrum for microparticles (III) containing a mixture of dyes used for A and B (solid line), in comparison with the spectrum of the FITC bead target material (dashed line).

A mixture of compounds 7 and 8 is prepared from 1.2 mL of compound 8 and 1.1 mL of compound 7 combined in 0.69 mL of $CH_2Cl_2$, and 1.10 mL of the dye mixture is added dropwise while stirring to 1 mL of 3% 5.1 μm polystyrene beads (Bangs) that have been washed with pure MeOH and pelleted. After stirring for 20 minutes, beads are spun down and excess dye mixture is removed. After washing with 2 mL MeOH three times, then with 2 mL 0.05% Tween 20 in water three times, beads are suspended in 0.05% Tween 20 in water. As indicated in FIG. 3B, the emission spectrum of the microparticles (III) that incorporate both compounds 7 and 8 substantially matches the emission spectrum of the FITC bead.

Example 5

Fluorescent Indicator Bead

5-Carboxy-2',7'-dichlorofluorescein diacetate (Molecular Probes, Inc., Eugene Oreg.) is dissolved in 20 mL $CH_2Cl_2$ to give a clear solution. The stirred solution is cooled to 0° C. and 0.43 g (4.36 mmoles) triethylamine is added. After five minutes, 0.64 g (4.67 mmoles) isobutyl chloroformate is added and the reaction is stirred at 20° C. for three hours, at which time TLC analysis shows that the starting acid has been completely converted to the mixed anhydride. The solvent is evaporated and redissolved in ethyl acetate. The colorless triethylamine hydrochloride is filtered and the clear filtrate is evaporated at 15° C. to give a colorless oil which dries to a foam under high vacuum. The yield is 2.2 g (3.5 mmoles; 90% yield).

11.0 g (17.7 mmoles) of 5,5'-dinitro BAPTA tetramethyl ester (CELL CALCIUM 10, 491 (1989)) is dissolved in 200 mL dimethylformamide and the solution is hydrogenated at 40 psi for three hours in the presence of 0.8 g 10% palladium on charcoal. When complete, the reaction is filtered through diatomaceous earth. The clear filtrate is diluted to 500 mL with ethyl acetate and the solution is washed three times with saturated NaCl and once with water. The organic layer is dried over $Na_2SO_4$ and evaporated under reduced pressure to a grey oil. Trituration with methanol yields 7.0 g (12.4 mmoles; 70.3% yield) of 5,5'-diamino BAPTA, tetramethyl ester (Compound XVI), ~95% pure by TLC in 5% methanol:$CHCl_3$.

5,5'-Diamino BAPTA tetramethyl ester (0.35 g, 0.64 mmoles) is dissolved in 5 mL dichloromethane. One equivalent of the mixed anhydride of 5-carboxy-2',7'-dichlorofluorescein diacetate (0.43 g, 0.64 mmoles) is added as a solid in three portions over ~10 min. The reaction is stirred at room temperature for three hours, then is stored in an ice bath overnight. TLC using 5% MeOH/$CHCl_3$ shows a new, ninhydrin positive quenching product formed with an $R_f$ of ~0.3. The reaction mixture is loaded directly onto a column packed with 150 mL silica (40–70 μ) and eluted with 3% MeOH/$CHCl_3$. The purest fractions are combined and evaporated to a light yellow oil (Compound XX).

A suspension of 0.13 g (0.13 mmoles) of Compound XX in 10 mL acetone is treated with 10 μL (0.14 mmoles) thiophosgene for 30 minutes at 30° C. The light yellow solution gives two products $R_f$ ~0.9 and $R_f$ ~0.5 in 1% AcOH:9% MeOH:$CHCl_3$. Both products are nearly colorless. The solution is evaporated to a light oil and triturated with 10 mL methanol. The suspension is centrifuged to give a tan solid that is redissolved in $CHCl_3$ and evaporated to 125 mg (88% yield) of the lower $R_f$ product, which reacts with n-butyl amine to give a new product on TLC. The new product (Compound XXII) is a conjugate of BAPTA with 2', 7'-dichlorofluorescein linked by a carboxamide linkage, having a reactive isothiocyanate group.

Compound XXII (30 mg, 0.028 mmoles) is dissolved in 1 mL dimethylformamide and is added in one portion to a stirring solution of 0.18 g (2.6 μmoles) 70,000 MW amino dextran (approximately 14 moles of amines/70,000 g of dextran, Molecular Probes, Inc.; Eugene Oreg.) in 2 mL DMSO. The reaction is stirred overnight at room temperature. The reaction solution is added to 100 mL vigorously stirring acetone to precipitate the product. The solid is filtered through a flitted glass funnel and the red solid is redissolved in 10 mL deionized water. To hydrolyze the methyl esters on the BAPTA chelator the pH is continuously maintained at 11.0 by addition of 40% KOH solution until the pH remains stable (~18 hours). The pH is readjusted with HCl to 8.0 and the solution is transferred to a dialysis membrane tubing with a 12–14,000 MW cutoff and dialyzed for two days versus deionized water. The orange solution is then lyophilized to give 0.16 g (0.3 μmoles, 89% yield) of CG indicating dextrans as an orange solid.

Figure 4B:
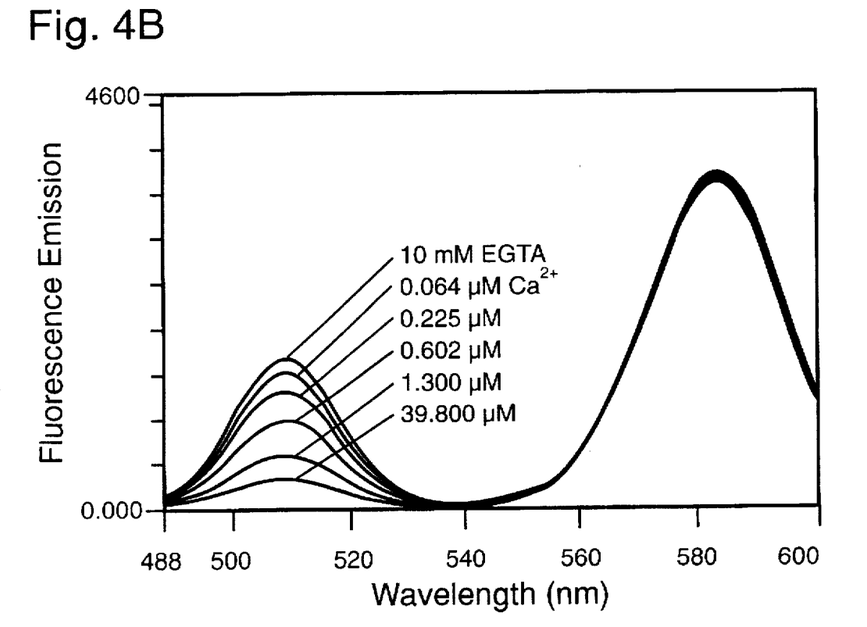
FIG. 4B shows the fluorescence emission response of 14 nm microparticles labeled with Compound 4, which exhibits a red emission, and the non-ratioable calcium ion indicator, which exhibits a variable green emission in response to $Ca^{2+}$ concentration. The excitation and emission spectra of the bead are scanned synchronously to give a ratioable response to calcium ion concentrations over the relevant physiological range.

Carboxylate-modified 14 nm polystyrene microparticles (Interfacial Dynamics) are labeled with Compound 4 according to Example 1. Using an approximate ratio of CG indicating dextrans to carboxyl groups on the microparticles of 2:1, the coupling of the flee amine groups on the CG indicating dextran to the surface of microparticles is performed as in Example 2. The excess dextran is then dialyzed out using dialysis tubing 500,000 MW cutoff. The fluorescence spectra of dipyrrometheneboron difluoride labeled beads containing the CG indicating dextrans are measured in CaEGTA solutions containing different concentrations of free calcium. The calcium ion solutions are prepared from 10 mM CaEGTA which, in 100 mM KCl and 10 mM 3-(N-morpholino)propane-sulfonic acid (MOPS) at 22° C. and 7.2 pH, contains 39.8 μM free calcium. Synchronous scanning of excitation and emission of the doubly-labeled beads in solution gives a ratioable response to the calcium ion concentration (FIG. 4B).

It is to be understood that, while the foregoing invention has been described in detail by way of illustration and example, only the preferred or specific embodiments have been revealed, and that numerous modifications, substitutions, and alterations are all permissible without departing from the spirit or scope of the invention as described in the following claims.

What is claimed is:

1. A fluorescent labeled material having enhanced photostability and quantum yield comprising at least one polymer microparticle less than about 50 micrometers in diameter that internally incorporates a fluorescent dipyrromethenenboron difluoride derivative compound of the general formula:

wherein X is $CR^4$, and where $R^1$–$R^7$, which may be the same or different, are hydrogen, halogen, alkyl, alkoxy, aryl, arylalkyl, cycloalkyl, acyl, formyl, or heteroaryl.

2. The material, as claimed in claim 1, wherein said polymer microparticle comprises polyurethane or polymerized monomers selected from a group consisting of styrene, bromostyrene, acrylic acid, acrylonitrile, acrylamide, methyl methacrylate, vinyl chloride, vinyl benzyl chloride, vinyl acetate, vinyl toluene, vinyl pyridine, vinylidene chloride, divinyl benzene, butadiene, and isoprene.

3. The material, as claimed in claim 1, wherein said microparticle is a polystyrene microparticle between 0.01 micrometers and 15 micrometers in diameter.

4. The material, as claimed in claim 1, further comprising at least one and not more than six additional dyes that are dipyrromethenenboron difluoride dyes.

5. The material, as claimed in claim 4, wherein at least one of said additional dyes is fluorescent.

6. The material, as claimed in claim 1, further comprising a bioreactive substance that is covalently attached or non-covalently adsorbed onto the microparticle.

7. The material, as claimed in claim 6, wherein said bioreactive substance is a drug.

8. The material, as claimed in claim 6, wherein said bioreactive substance is a biomolecule.

9. The material, as claimed in claim 8, wherein said biomolecule is a carbohydrate.

10. The material, as claimed in claim 8, wherein said biomolecule is a peptide or protein.

11. The material, as claimed in claim 8, wherein said biomolecule is an antibody.

12. The material, as claimed in claim 8, wherein said biomolecule is biotin, avidin or streptavidin.

13. The material, as claimed in claim 8, wherein said biomolecule is a nucleic acid compound.

14. A fluorescent labeled material having enhanced photostability and quantum yield comprising at least one polymeric microparticle less than 50 micrometers in diameter; wherein said polymer microparticle comprises polyurethane or polymerized monomers selected from a group consisting of styrene, bromostyrene, acrylic acid, acrylonitrile, acrylamide, methyl methacrylate, vinyl chloride, vinyl benzyl chloride, vinyl acetate, vinyl toluene, vinyl pyridine, vinylidene chloride, divinyl benzene, butadiene, and isoprene; in which is internally incorporated without covalent attachment at least one fluorescent dye that is a dipyrromethenenboron difluoride dye.

15. The material, as claimed in claim 14, wherein said microparticle further comprises a surface functional group selected from a group consisting of sulphate, phosphate, hydroxyl, carboxyl, ester, amide, amidine, amine, sulfhydryl, and aldehyde.

16. A material, as claimed in claim 14, further comprising a bioreactive substance that is covalently attached or non-covalently adsorbed onto the microparticle.

17. A material, as claimed in claim 14, wherein the polymeric microparticle is a polystyrene microparticle having a diameter between about 0.01 micrometers and about 15 micrometers.

18. A material, as claimed in claim 14, further comprising at least one and no more than six additional dipyrromethenenboron difluoride dyes.

19. A material, as claimed in claim 18, further comprising a biomolecule that is a peptide, protein, carbohydrate or nucleic acid compound.

20. A fluorescent labeled material having enhanced photostability and quantum yield comprising at least one polymeric microparticle less than about 50 micrometers in diameter in which is internally incorporated without covalent attachment, at least one fluorescent dye that is a dipyrromethenenboron difluoride derivative compound of the general formula:

wherein $R^1$–$R^7$, which may be the same or different, are hydrogen, halogen, alkyl, alkoxy, aryl, arylalkyl, cycloalkyl, acyl, formyl, cyano, alkenyl, or heteroaryl, or adjacent substituents $R^2$ and $R^3$ or $R^5$ and $R^6$ or both $R^2$ and $R^3$ and $R^5$ and $R^6$ combine to form 1 or 2 fused unsaturated ring substituent(s).

21. A material, as claimed in claim 20, wherein according to the formula of said fluorescent dye: $R^4$ is hydrogen, $C_1$–$C_{10}$ alkyl, aryl, or heteroaryl; $R^2$ and $R^6$ are hydrogen or lower alkyl; $R^1$, $R^3$, $R^5$, and $R^7$ are independently hydrogen, aryl, heteroaryl, or $C_1$–$C_{10}$ alkyl.

22. A material, as claimed in claim 21, wherein according to the formula of said fluorescent dye, any heteroaryl substituent of the fluorescent dye is a pyrrole, thiophene, furan, oxazole, isoxazole, oxadiazole, imidazole, benzoxazole, benzothiazole, benzimidazole, benzofuran or indole substituent.

23. A material, as claimed in claim 22, wherein the microparticle is a polystyrene microparticle having a diameter between 0.01 micrometers and 15 micrometers.

24. A material, as claimed in claim 20, wherein the microparticle further comprises one to six additional fluorescent dyes that are dipyrromethenenboron difluoride dyes.

25. A material, as claimed in claim 24, wherein one or more additional fluorescent dyes are simultaneously or sequentially internally incorporated without covalent attachment and each additional fluorescent dye that is internally incorporated is a dipyrrometheneboron difluoride dye that has the formula:

wherein X is N or $CR^4$, and where any or all of the substituents $R^1$–$R^7$, of the additional fluorescent dye, which may be the same or different, are an aryl, alkenyl, or heteroaryl group, or adjacent substituents $R^2$ and $R^3$ or $R^5$ and $R^6$ or both $R^2$ and $R^3$ and $R^5$ and $R^6$ combine to form 1 or 2 fused unsaturated ring substituent(s); or are hydrogen, alkyl, alkoxy, arylalkyl, cycloalkyl, acyl, formyl, or cyano.

26. A material, as claimed in claim 25, the microparticle has an emission wavelength distribution curve that substantially matches an emission wavelength distribution curve of a target material.

27. A material, as claimed in claim 26, the microparticle has an emission wavelength distribution curve that substantially matches an emission wavelength distribution curve of a target material that contains a fluorescein, a rhodamine, a carbocyanine, a natural pigment, or a nucleic acid stain.

28. A material, as claimed in claim 24, further comprising an additional fluorescent dye that is an enzyme substrate and is externally attached to the microparticle.

29. A material, as claimed in claim 24, further comprising an additional dye that is a fluorescent indicator of pH or a metal ion and is externally attached to the microparticle.

30. A material, as claimed in claim 20, further comprising a bioreactive substance.

* * * * *